US006642366B1

(12) United States Patent
Scheinmann et al.

(10) Patent No.: US 6,642,366 B1
(45) Date of Patent: Nov. 4, 2003

(54) PROCESS FOR MAKING MORPHINE-6-GLUCURONIDE AND ITS ANALOGUES USING HALOGLUCURONATE ESTER INTERMEDIATES

(75) Inventors: Feodor Scheinmann, Cheshire (GB); Andrew Valentine Stachulski, Lancashire (GB); John Ferguson, Manchester (GB); Jane Louise Law, Manchester (GB)

(73) Assignee: UFC Limited, Manchester (GB)

( * ) Notice: Subject to any disclaimer, the term of this patent is extended or adjusted under 35 U.S.C. 154(b) by 0 days.

(21) Appl. No.: 10/019,585

(22) PCT Filed: Jun. 20, 2000

(86) PCT No.: PCT/GB00/02232

§ 371 (c)(1),
(2), (4) Date: Jun. 7, 2002

(87) PCT Pub. No.: WO00/78764

PCT Pub. Date: Dec. 28, 2000

(30) Foreign Application Priority Data

Jun. 21, 1999 (GB) ............................................. 9914382

(51) Int. Cl.[7] ........................ C07H 15/00; C07H 15/24; C07D 489/02
(52) U.S. Cl. .................... 536/17.4; 536/18.5; 536/18.1; 536/18.4; 536/115; 536/122; 536/124
(58) Field of Search ............... 536/17.4, 18.5, 536/115, 18.4, 122, 124, 18.1

(56) References Cited

U.S. PATENT DOCUMENTS 5,218,097 A * 6/1993 Beat
5,621,087 A * 4/1997 Scheinmann et al.

* cited by examiner

Primary Examiner—Samuel Barts
Assistant Examiner—Michael C. Henry
(74) Attorney, Agent, or Firm—Notaro & Michalos P.C.

(57) ABSTRACT

A process for manufacturing morphine-6-glucuronide and related compounds of the general structure of Formula 1:

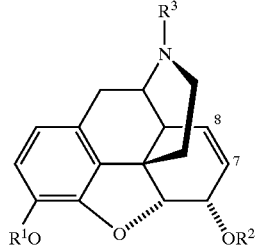

Formula 1 wherein optionally substituted morphine is conjugated with an optionally substituted member of a new class of intermediates, namely, 1-haloglucuronate esters, in the presence of iodine or an iodinium compound. The conjugation may be followed by conversion of $R^1$ of Formula 1 into hydrogen and/or the removal of the ester groups from the glucuronic residue at $R^2$ of Formula 1.

17 Claims, No Drawings

PROCESS FOR MAKING MORPHINE-6-GLUCURONIDE AND ITS ANALOGUES USING HALOGLUCURONATE ESTER INTERMEDIATES

This is the National Phase Application of PCT/GB 00/02232 filed, Jun. 20, 2000.

The present invention relates to a process for the manufacture of morphine-6-glucuronide (M6G) and its analogues and also to new intermediates for their manufacture.

Morphine and its known derivatives are opiates which have pain relief properties and are therefore useful in the treatment of chronic and acute pain encountered in various indications in human and other warm blooded animals. Certain known derivatives may also be used as antidotes in situations of abuse or overdose.

Some Morphine derivatives are described in published patent specifications WO 93/03051, WO 95/16050, and also in patent application PCT/GB 98/01071, the disclosures of which are incorporated herein by way of reference.

In particular, WO 93/03051 describes various substituted morphine-6-glucuronide derivatives, and also various substituted glucuronate ester derivatives useful as intermediates in the manufacture of the morphine-6-glucuronide derivatives.

PCT/GB 98/01071 describes a specific selected range of substituted morphine-6-glucuronide derivatives wherein a C(7)–C(8) linkage of the molecule is di-hydro or otherwise saturated rather than being an ethylenic double bond.

These references also disclose particular advantageous new processes for the preparation of morphine derivatives which avoid the use of heavy metals such as silver and barium described previously by H. Yoshimura et al., *Chem. Pharm. Bull.*, 1968, 16, 2114, and P. A. Carrupt. et al., *J. Med. Chem.*, 1991, 34, 1272 using the Koenigs-Knorr procedure. As described in WO 93/0305, morphine-6-glucuronide can be prepared by conjugating a morphine derivative with a glucuronic acid ester or imidate in the presence of acid catalysis. In the process described in WO 95/16050 the 3-glucuronide moiety in morphine-3,6-glucuronide or substituted morphine-6-glucuronide is subjected to selective enzymatic cleavage using at least one β-glucuronidase. The avoidance of heavy metals permits production of morphine-6-glucuronide and its derivatives devoid of heavy metals which allows the products to be made available for pharmaceutical use.

An object of the present invention is to provide a process, which can employ cheaper reagents and reactants in equimolar amounts, for making M6G and dihydro M6G and related compounds of the following general formula, in which $R^1$, $R^2$ and $R^3$ are defined below:

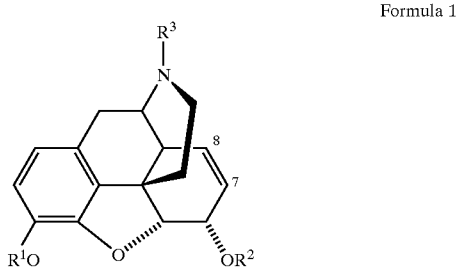

Formula 1

$R^1$=alkyl both branched and un-branched, aryl, silyl or acyl $R^2$=glycoside ester $R^3$=alkyl, aryl, hydrogen or $(CH_2)_nX$ where n is an integer and $X=NRR^4$ where R and $R^4$ are hydrogen, alkyl, aryl or acyl.

The C(7)–C(8) linkage may be olefin or dihydro or olefin adducts CHX-CHY (X,Y=epoxy, halogen, hydrohalogen).

The present invention is based on the use of new intermediates which have been prepared, namely 1-iodo derivatives of glucuronate esters. Glycosyl iodides previously have been regarded as unstable and unsuitable as intermediates in synthesis (R. J. Ferrier in *Carbohydrate Chemistry*, ed. J. F. Kennedy, OUP, 1984, 448. P. M. Collins and R. J. Ferrier, *Monosaccharides*, Wiley, 1995, 163).

The method of the invention consists of the conjugation of an optionally substituted 1-haloglucuronate ester, preferably the 1-iodo derivative, with morphine or substituted morphine, using iodine or an iodonium reagent. This may be followed by a conversion of $R^1$ in Formula 1 into hydrogen and as appropriate the removal of the ester groups from the glucuronic residue at $R^2$ (Formula 1).

Preferred substituents $R^1$, $R^2$ and $R^3$ of the optionally substituted product M6G are given in the following table 1. The preferred substituents $R^1$, $R^2$ and $R^3$ for the morphine component used in the process are:

$R^1$=H; acyl, especially acetyl, benzoyl, isobutyryl or pivaloyl; trialkylsilyl, especially t-butyldimethylsilyl; lower alkyl, especially methyl; and methyl β-D-(2,3,4-tri-O-acyl) glucuronate $R^2$=H $R^3$=methyl, methyl N-oxide ($N^{Me}$) or $(CH_2)_nX$ where $X=NRR^4$, R and $R^4$ being H, alkyl, aryl or acyl; OR or halogen, and the C(7)–C(8) linkage may be olefin, dihydro or olefin adducts CHX-CHY (X,Y=epoxy, halogen, hydrohalogen).

TABLE 1

| $R^1$ | $R^2$ | $R^3$ |
|---|---|---|
| H | β-D-glucuronyl | methyl |
| β-D-glucouronyl | β-D-glucuronyl | methyl |
| acetyl | methyl β-D-(2,3,4-tri-isobutyryl) glucuronate | methyl |
| benzoyl | methyl β-D-(2,3,4-tri-isobutyryl) glucuronate | methyl |
| H | methyl β-D-(2,3,4-tri-isobutyryl) glucuronate | methyl |
| tbutyldimethylsilyl | methyl β-D-(2,3,4-tri-isobutyryl) glucuronate | methyl |
| isobutyryl | methyl β-D-(2,3,4-tri-isobutyryl) glucuronate | methyl |
| pivaloyl | methyl β-D-(2,3,4-tri-pivalyl) glucuronate | methyl |
| methyl β-D-(2,3,4-tri-acetyl) glucuronate | acetyl | methyl |
| methyl β-D-(2,3,4-tri-acetyl) glucuronate | methyl β-D-(2,3,4-tri-acetyl) glucuronate | methyl |
| methyl β-D-(2,3,4-tri-isobutyryl) glucuronate | methyl β-D-(2,3,4-tri-isobutyryl) glucuronate | methyl |
| methyl | β-D-glucuronyl | methyl |
| H | β-D-glucuronyl | methyl, → O |
| H | β-D-glucuronyl | $(CH_2)_nX$ where X = $NRR^4$, R and R4 being H, alkyl, aryl or acyl; OR or halogen |
| pivaloyl | methyl-β-D-(2,3,4-tri-O-acetyl) glucuronate | methyl |
| pivaloyl | methyl-β-D-(2,3,4-tri-O-isobutyryl) glucuronate | methyl |

TABLE 1-continued

| R¹ | R² | R³ |
|---|---|---|
| methyl β-D-(2,3,4-tri-O-pivaloyl) glucuronate | methyl-β-D-(2,3,4-tri-O-pivaloyl) glucuronate | methyl |

The 1-haloglucuronate ester and substituted versions thereof as used in the process of the invention may have the following formula:

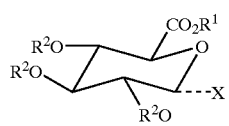

Formula 2 in which:

R¹=alkyl or aryl, preferably methyl

R²=acyl, silyl, alkyl, benzyl or aryl, preferably acetyl, isobutyryl or pivaloyl and X=halogen in the α or β configuration, preferably Br or I, more preferably I.

Specific examples (which are not limiting) of the preparations of these compounds are given below. In a preferred embodiment of the present invention the phenolic group of the M6G or substituted M6G is protected. The protected esters may then be isolated followed by chemical or enzymic hydrolysis or cleavage to liberate the free M6G or substituted M6G, Preparations of the compounds of the type shown in Formula 2 in which X=O-acyl are well known in the literature (G. N. Bollenback et al., *J. Am. Chem. Soc.*, 1955, 77, 3310; J. Vlahov and G. Snatzke, *Liebigs Ann. Chem.*, 1983, 570; WO 93/03051).

A tetraacyl derivative of this kind may then be converted to the desired 1-halo derivative by treatment with a hydrogen halide (especially HBr), as described in the above references, or more conveniently in the case where X=I is required, by treatment with a Lewis acid and an alkali metal iodide as described for the case R¹=Me, R²=MeCO (R. T. Brown et al., *J. Chem. Res.* (S), 1997, 370) and further exemplified in a non-limiting manner below.

The 1-halosugar derivative may then be condensed with a morphine derivative, in which the phenolic OH group is protected as defined in WO 93/03051, by using elemental iodine or an iodonium derivative such as IBr, ICl or N-iodosuccinimide. This coupling method is very mild and has the advantage that good yields of product are obtained at 1:1 molar ratios of morphine component to carbohydrate; large excesses of carbohydrate are unnecessary, simplifying the workup of the reaction and in particular reducing the need for chromatography. The iodine may be advantageously combined with a promoter or co-catalyst, preferably a Lewis acid, e.g. a Group I, II, III or a transition metal halide such as ZnI₂, MgI₂, FeCl₃ or using ICl or IBr themselves as co-catalysts.

The use of iodine to catalyse glycosidation of alcohols using various bromosugars in the glucose series was reported by R. A. Field et al., *Tetrahedron Letters.*, 1996, 37, 8807. There has however been no realisation of the techniques of the present invention and in particular:

1) the use of iodonium catalysts IBr, ICl and N-iodosuccinimide (NIS) has received little attention (in the case of IBr) and none in the case of ICl or NIS;

2) addition of a glucuronic acid residue is recognised by experts in carbohydrate chemistry as a very demanding process; coupling methods which work with other monosaccharides may be quite ineffective with the corresponding glucuronic acid derivatives (R. R. Schmidt et al., *Tetrahedron Lett.*, 1994, 35, 4763). Indeed, here, iodine itself can be a poor promoter of the coupling of a glucuronic acid derivative of Formula 2 with X=α-Br and the more active promoters may be appropriate in this case;

3) the use of an iodosugar in conjunction with iodine promotion is without precedent.

The process disclosed herein is suitable for the synthesis of a large number of new compounds related to M6G corresponding to the following formula (which is Formula 1):

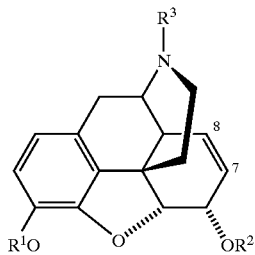

Formula 1 wherein, positions 7, 8 can be olefin as shown or dihydro-, dihydroxy-, hydroxyhalo-, epoxy-, dihalo-, hydrohalo-, hydrohydroxy-, or CXY (X, Y=halogen or hydrogen) adducts;

and wherein R¹, R² and R³ may be any of the combinations of Table 1.

Also new sugars included in Formula 2 may be used as intermediates, as follows:

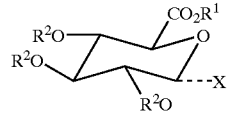

Formula 2 in which:

R¹=methyl

R²=isobutyryl or pivaloyl

X=I

EXAMPLES

The following examples describe representative preparations of the sugar intermediates and their conjugation to suitable morphine derivatives.

1) Preparation of Methyl 1-Deoxy-1-iodo-2.3.4-tri-O-pivaloyl-α-D-glucopyranuronate Methyl 1,2,3,4-tetra-O-pivaloyl-β-D-glucopyranuronate (2.72 g, 5 mmol) in acetonitrile (10 cm³) was heated and stirred at gentle reflux under argon with potassium iodide (1.66 g, 10 mmol) and boron trifluoride diethyl etherate (2.50cm³). After 1 h the dark mixture was cooled, then 10% aq. sodium thiosulfate (25 cm³) and saturated aqueous sodium bicarbonate (NaHCO₃) (25 cm³) were added and the product was extracted using ethyl acetate (50 cm³+20 cm³). The combined organic phases were washed with further NaHCO₃, water and brine, then dried over anhydrous Na₂SO₄ and evaporated to an orange gum (2.8 g). Triuration with ethanol gave a crystalline product; evaporation of the mother liquors, followed by chromatography on silica gel, eluting with 10% ethyl acetate in hexane, afforded further product of equal purity; combined yield, 1.89 g (66%), m.p. 98–100° C.; $\delta_H$ (220 MHz, CDCl$_3$) 1.10–1.30 (27H, 3s), 3.73 (3H, s), 4.26 (1H, dd), 4.35 (1H, d), 5.22, 5.61 (2H, 2t) and 7.04 (1H, d).

2) Preparation of Methyl 1-(3-O Pivaloylmorphin-6-yl)-2.3.4-tri-O-pivaloyl-β-D-glucopyranuronate 3-O-Pivaloylmorphine (0.185 g, 0.5 mmol) and the iodosugar described in 1) (0.286 g, 0.5 mmol) were stirred at 20° C. with iodine (0.35 g, 1.38 mmol) in 1,2-dichloroethane (2 cm$^3$) over 4 Å molecular sieves with exclusion of light. After 64 h the reaction mixture was diluted with ethyl acetate (25 cm$^3$) and washed sequentially with 10% aq. sodium thiosulfate (back-washing with 10 cm$^3$ ethyl acetate), 5% aq. citric acid, 0.5M sodium hydroxide, water and brine. Following drying over sodium sulphate and evaporation (giving 0.53 g of crude product), chromatography on silica gel was performed, eluting firstly with ethyl acetate: hexane, 1:2, then with dichloromethane (DCM), followed by 4% methanol in DCM and finally 10% methanol in DCM. Appropriate fractions (ultraviolet absorbing and stained red by iodoplatinate) were combined and evaporated to give the title product (0.232 g, 57%) whose $^1$H NMR spectrum was identical to that of material prepared by the acid catalysed process of WO 93/03051.

It is of course to be understood that the invention is not intended to be restricted to the details of the above Examples which are described for the purposes of illustration only.

What is claimed is:

1. A process for the production of compounds of the general structure of Formula 1:

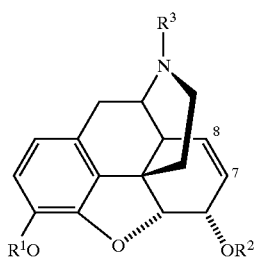

Formula 1 in which:
R$^1$=alkyl both branched and unbranched, aryl, allyl or acyl;
R$^2$=glycoside ester;
R$^3$=alkyl, aryl, hydrogen or (CH$_2$)$_n$X, where n is an integer and X=NRR$^4$, where R and R$^4$ are hydrogen, alkyl, aryl or acyl; and in which the C(7)–C(8) linkage is olefin, dihydro, dihydroxy, hydroxyhalo, epoxy, dihalo, hydrohalo, hydrohydroxy, or olefin adducts CHX-CHY, where X and Y are epoxy, halogen or hydrohalogen;
comprising conjugating 1-iodoglucuronate ester or a substituted 1-iodoglucuronate ester with morphine or substituted morphine in the presence of iodine or an iodonium compound;
said substituted 1-iodoglucuronate ester having the general structure shown in Formula 2:

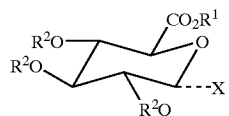

Formula 2 in which:
R$^1$=alkyl or aryl;
R$^2$=acyl, silyl, alkyl, benzyl or aryl;
X=iodine in the α or β configuration; and
said substituted morphine having the general structure of Formula 1 in which:
R$^1$=hydrogen, acyl, trialkylsilyl, lower alkyl, or methyl-β-D-(2,3,4-tri-O-acyl)glucuronate;
R$^2$=hydrogen;
R$^3$=methyl, methyl N-oxide (N$^{Me}_o$), or (CH$_2$)$_n$X, where X=NRR$^4$, R and R$^4$ each being one of hydrogen, alkyl, aryl, acyl and a halogen.

2. A process according to claim 1, wherein said conjugation is followed by converting R$^1$ of the compound of Formula 1 into hydrogen.

3. A process according to claim 1, wherein the conjugating is followed by removing ester groups from glucuronic residue at R$^2$ of the compound of Formula 1.

4. A process according to claim 1, wherein R$^1$, R$^2$, and R$^3$ of the compound of Formula 1 are selected from the group of combinations consisting of:

a) R$^1$ is H, R$^2$ is β-D-glucuronyl, and R$^3$ is methyl;
b) R$^1$ is β-D-glucuronyl, R$^2$ is β-D-glucuronyl and R$^3$ is methyl;
c) R$^1$ is acetyl, R$^2$ is methyl β-D-(2,3,4-triisobutyryl) glucuronate, and R$^3$ is methyl;
d) R$^1$ is benzoyl, R$^2$ is methyl β-D-(2,3,4-triisobutyryl) glucuronate, and R$^3$ is methyl;
e) R$^1$ is H, R$^2$ is methyl β-D-(2,3,4-triisobutyryl) glucuronate, and R$^3$ is methyl;
f) R$^1$ is butyldimethylsilyl, R$^2$ is methyl β-D-(2,3,4-triisobutyryl) glucuronate, and R$^3$ is methyl;
g) R$^1$ is isobutyryl, R$^2$ is methyl β-D-(2,3,4-triisobutyryl) glucuronate, and R$^3$ is methyl;
h) R$^1$ is pivaloyl, R$^2$ is methyl β-D-(2,3,4-tripivalyl) glucuronate, and R$^3$ is methyl;
i) R$^1$ is methyl β-D-(2,3,4-triacetyl) glucuronate, R$^2$ is acetyl and R$^3$ is methyl;
j) R$^1$ is methyl β-D-(2,3,4-triacetyl) glucuronate, R$^2$ is methyl β-D-(2,3,4-triacetyl) glucuronate and R$^3$ is methyl;
k) R$^1$ is methyl β-D-(2,3,4-triisobutyryl) glucuronate, R$^2$ is methyl β-D-(2,3,4triisobutyryl) glucuronate and R$^3$ is methyl;
l) R$^1$ is methyl, R$^2$ is β-D-glucuronyl and R$^3$ is methyl;
m) R$^1$ is H, R$^2$ is β-D-glucuronyl and R3 is methyl;
n) R$^1$ is H, R$^2$ is β-D-glucuronyl and R$^3$ is (CH2)$_n$X Where X=NRR$^4$, R and R$^4$ being H, alkyl, aryl or acyl; or halogen;
o) R$^1$ is pivaloyl, R$^2$ is methyl β-D-(2,3,4-tri-O-acetyl) glucuronate and R$^3$ is methyl;
p) R$^1$ is pivaloyl, R$^2$ is methyl β-D-(2,3,4-tri-O-isobutyryl) glucuronate and R$^3$ is methyl; and
q) R$^1$ is methyl 1-D-(2,3,4-tri-O-pivaloyl) glucuronate, R$^2$ is methyl β-D-(2,3,4-tri-O-pivaloyl) glucuronate and R$^3$ is methyl.

5. A process according to claim 1, wherein $R^1$ of the substituted morphine is one of acetyl, benzoyl, isobutyryl and pivaloyl.

6. A process according to claim 1, wherein $R^1$ of the substituted morphine is t-butyldimethylsilyl.

7. A process according to claim 1, wherein $R^1$ of the substituted morphine is methyl.

8. A process according to claim 1, wherein $R^1$ of Formula 2 is methyl.

9. A process according to claim 1, wherein $R^2$ of Formula 2 is one of acetyl, isobutyryl and pivaloyl.

10. A process according to claim 1, wherein the phenolic-OH group of the compound of Formula 1 is reversibly protected.

11. A process according to claim 1, wherein the said iodonium compound is one of IBR, ICI or N-iodosuccinimide.

12. A process according to claim 1, wherein the said iodine or iodonium compound is combined with a co-catalyst.

13. A process according to claim 12, wherein the co-catalyst is a Lewis acid.

14. A process according to claim 13, wherein the Lewis acid is one of a group I, II, III and transition metal halide.

15. A process according to claim 12, wherein the co-catalyst is a second iodonium compound.

16. 1-iodo-derivatives of glucuronate esters having the general structure of Formula 2:

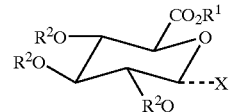

Formula 2 wherein:
$R^1$=alkyl or aryl;
$R^2$=isobutyryl, pivaloyl, silyl, alkyl, benzyl or aryl;
X=iodine in the α or β configuration.

17. 1-iodo-derivatives of glucuronate esters according to claim 16, wherein $R^1$ is methyl.

* * * * *